United States Patent
Watanabe et al.

(10) Patent No.: US 10,308,604 B2
(45) Date of Patent: Jun. 4, 2019

(54) METHOD FOR PRODUCING PYRROLE DERIVATIVE, AND INTERMEDIATE THEREOF

(71) Applicant: Daiichi Sankyo Company, Limited, Chuo-ku, Tokyo (JP)

(72) Inventors: Masashi Watanabe, Hiratsuka (JP); Hiroshi Nagasawa, Fujisawa (JP); Noritada Sato, Hiratsuka (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/950,973

(22) Filed: Apr. 11, 2018

(65) Prior Publication Data

US 2018/0230095 A1    Aug. 16, 2018

Related U.S. Application Data

(60) Division of application No. 15/699,954, filed on Sep. 8, 2017, now Pat. No. 10,005,725, which is a division of application No. 15/043,260, filed on Feb. 12, 2016, now Pat. No. 9,765,025, which is a continuation of application No. PCT/JP2014/072332, filed on Aug. 26, 2014.

(30) Foreign Application Priority Data

Aug. 27, 2013 (JP) ................................. 2013-175172

(51) Int. Cl.
| | |
|---|---|
| C07B 57/00 | (2006.01) |
| C12P 17/10 | (2006.01) |
| C12P 41/00 | (2006.01) |
| C07D 207/34 | (2006.01) |
| C07D 207/456 | (2006.01) |

(52) U.S. Cl.
CPC ............ *C07D 207/34* (2013.01); *C07B 57/00* (2013.01); *C07D 207/456* (2013.01); *C12P 17/10* (2013.01); *C12P 41/005* (2013.01)

(58) Field of Classification Search
CPC .................................................. C07D 207/34
See application file for complete search history.

(56) References Cited

U.S. PATENT DOCUMENTS

| | | | |
|---|---|---|---|
| 8,524,918 | B2 | 9/2013 | Aoki et al. |
| 8,754,118 | B2 | 6/2014 | Aoki et al. |
| 2011/0263673 | A1 | 10/2011 | Nuss et al. |

FOREIGN PATENT DOCUMENTS

| | | |
|---|---|---|
| CN | 101006052 A | 7/2007 |
| CN | 101679243 A | 3/2010 |
| EP | 2985277 A1 | 2/2016 |
| JP | 2010111657 A | 5/2010 |
| JP | 2012505225 A | 3/2012 |
| WO | 2006/012642 A2 | 2/2006 |
| WO | 2008/126831 A1 | 10/2008 |
| WO | 2010/098286 A1 | 9/2010 |
| WO | 2014168103 A1 | 10/2014 |

OTHER PUBLICATIONS

International Preliminary Report on Patentability and Written Opinion dated Mar. 1, 2016, issue in corresponding International Application No. PCT/JP2014/072332, filed Aug. 26, 2014, 8 pages.
International Search Report and Written Opinion dated Sep. 22, 2014, issue in International Application No. PCT/JP2014/072332, filed Aug. 26, 2014, 11 pages.
First Office Action dated Nov. 1, 2016, issued in Chinese Application No. 201480043766, filed Aug. 26, 2014, 8 pages.
Extended European Search Report dated Mar. 22, 2017, issued in Application No. EP14839943.9, filed Aug. 26, 2014, 8 pages.

*Primary Examiner* — Valerie Rodriguez-Garcia
(74) *Attorney, Agent, or Firm* — Christensen O'Connor Johnson Kindness PLLC

(57) ABSTRACT

The present invention provides a method for producing an atropisomer of a pyrrole derivative having excellent mineralocorticoid receptor antagonistic activity, and an intermediate thereof. A method for producing an atropisomer of a pyrrole derivative using a compound represented by (B) [wherein $R^1$ represents a C1-C4 alkyl group, and $R^2$ represents a 2-hydroxyethyl group or a carboxymethyl group] as a production intermediate.

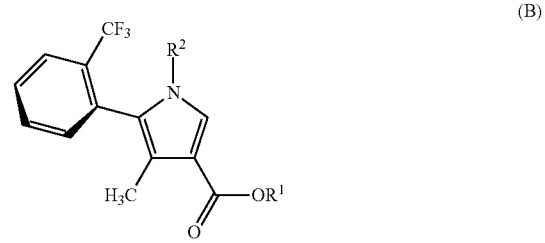

(B)

5 Claims, No Drawings

METHOD FOR PRODUCING PYRROLE DERIVATIVE, AND INTERMEDIATE THEREOF

CROSS-REFERENCES TO RELATED APPLICATIONS

This application is a division of U.S. application Ser. No. 15/699,954, filed Sep. 8, 2017, which is a division of U.S. application Ser. No. 15/043,260, filed Feb. 12, 2016, which is a continuation of International Application No. PCT/JP2014/072332, filed Aug. 26, 2014, which claims priority from Japanese Application No. 2013-175172, filed Aug. 27, 2013. Each application is incorporated herein by reference in its entirety.

TECHNICAL FIELD

The present invention relates to a method for producing an atropisomer of a pyrrole derivative having excellent mineralocorticoid receptor antagonistic activity, and a production intermediate thereof.

BACKGROUND ART

A mineralocorticoid receptor (MR) (aldosterone receptor) is known to play an important role in regulating electrolyte balance and blood pressure in the body, and MR antagonists having a steroidal structure such as spironolactone and eplerenone are known to be useful for the treatment of hypertension and heart failure.

1-(2-Hydroxyethyl)-4-methyl-N-[4-(methylsulfonyl)-phenyl]-5-[2-(trifluoromethyl) phenyl]-1H-pyrrole-3-carboxamide, which is a pyrrole derivative, is disclosed in PTL 1. Further, an atropisomer thereof is disclosed in PTL 2 and is known to be useful for the treatment of hypertension, diabetic nephropathy, and the like.

CITATION LIST

Patent Literature

PTL 1: WO 2006/012642 (US Patent Application No. US 2008-0234270)
PTL 2: WO 2008/126831 (US Patent Application No. US 2010-0093826)

SUMMARY OF INVENTION

Technical Problem

Substances to be used for pharmaceutical products are required to have particularly strictly high purity so as not to cause unpredicted side effects (for example, toxicity, etc.) due to their impurities. Further, in their industrial production methods (mass production methods), impurities are required to be removed by simpler operations.

In addition, it is important that pharmaceutical drug substances or production intermediates can be stored for long periods of time while maintaining their quality. In the case where it is necessary to store such substances under low temperature conditions, a large-scale refrigeration facility is needed for maintaining quality, and therefore, it is industrially meaningful to find stable crystals which can be stored at room temperature or higher.

Under such circumstances, the present inventors made intensive studies for developing a method for producing (S)-1-(2-hydroxyethyl)-4-methyl-N-[4-(methylsulfonyl)-phenyl]-5-[2-(trifluoromethyl) phenyl]-1H-pyrrole-3-carboxamide (hereinafter sometimes referred to as "Compound A)"), which is an atropisomer of a pyrrole derivative having excellent MR antagonistic activity, with higher quality in higher yield by using a more industrially advantageous operation method with lower environmental impact. As a result, they found a method for efficiently resolving an atropisomer of a novel synthetic intermediate, and based on this finding, they established a method for producing an atropisomer of a pyrrole derivative with high quality in high yield by using an industrially advantageous operation, and thus completed the present invention.

Solution to Problem

The present inventors intensively studied a production intermediate of an atropisomer of 1-(2-hydroxyethyl)-4-methyl-N-[4-(methylsulfonyl) phenyl]-5-[2-(trifluoromethyl) phenyl]-1H-pyrrole-3-carboxamide, which is a pyrrole derivative having excellent mineralocorticoid receptor antagonistic activity, and an efficient method for producing the same so as to improve solubility, purity, stability, and the like for enhancing the medical usefulness of the atropisomer of the pyrrole derivative.

Hereinafter, the present invention will be described in detail.

The present invention is directed to:

(1) a pyrrole compound represented by the following formula (B):

[Chem. 1]

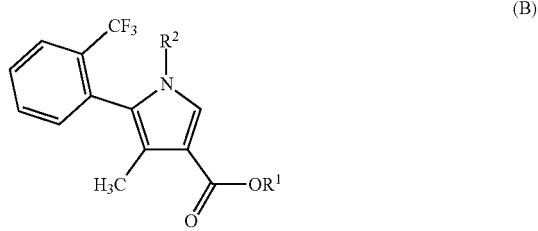

[wherein $R^1$ represents a C1-C4 alkyl group, and $R^2$ represents a 2-hydroxyethyl group or a carboxymethyl group];

(1-2) the pyrrole compound according to the above (1), wherein $R^1$ is an ethyl group;

(1-3) the pyrrole compound according to the above (1), wherein $R^2$ is a 2-hydroxyethyl group;

(1-4) the pyrrole compound according to the above (1), wherein $R^2$ is a carboxymethyl group;

(1-5) (S)-2-[4-ethoxycarbonyl-3-methyl-2-[2-(trifluoromethyl)phenyl]-1H-pyrrol-1-yl]acetic acid;

(2) ethyl (S)-1-(2-hydroxyethyl)-4-methyl-5-[2-(trifluoromethyl)phenyl]-1H-pyrrole-3-carboxylate represented by the following formula (Ia):

[Chem. 2]

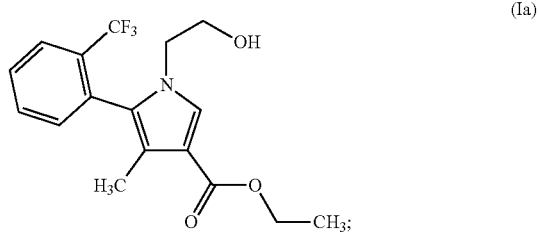

(3) a method for producing a compound represented by the following formula (Ib):

[Chem. 3]

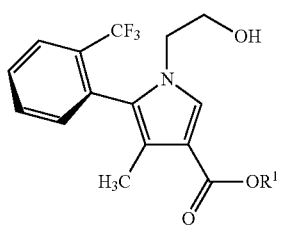

(Ib)

[wherein $R^1$ represents a C1-C4 alkyl group], characterized by resolving an atropisomer of the following formula (IB):

[Chem. 4]

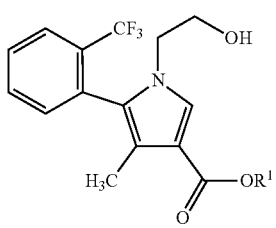

(IB)

in a solvent in the presence of an acyl donor using one enzyme selected from a lipase and a protease;

(4) a method for producing ethyl (S)-1-(2-hydroxyethyl)-4-methyl-5-[2-(trifluoromethyl)-phenyl]-1H-pyrrole-3-carboxylate represented by the following formula (Ia):

[Chem. 5]

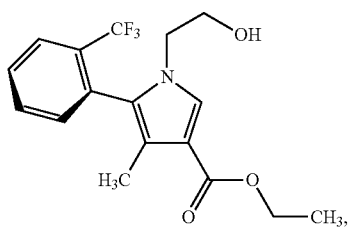

(Ia)

characterized by resolving an atropisomer of ethyl (RS)-1-(2-hydroxyethyl)-4-methyl-5-[2-(trifluoromethyl)-phenyl]-1H-pyrrole-3-carboxylate in a solvent in the presence of an acyl donor using one enzyme selected from a lipase and a protease;

(5) the method according to the above (3) or (4), wherein the enzyme is a lipase;

(6) the method according to the above (3) or (4), wherein the enzyme is an immobilized lipase;

(6-1) the method according to the above (6), wherein the immobilized lipase is one immobilized lipase selected from Chirazyme L-2, Chirazyme L-2 carrier-fixed C3, Chirazyme L-6 *Pseudomonas* sp., and Novozyme 435;

(6-2) the method according to any one selected from the above (4) to (6), wherein the acyl donor is vinyl propionate, vinyl acetate, vinyl butyrate, or vinyl laurate;

(7) the method according to the above (3) or (4), wherein the solvent is an organic solvent;

(8) a method for resolving an atropisomer of the following general formula (C):

[Chem. 6]

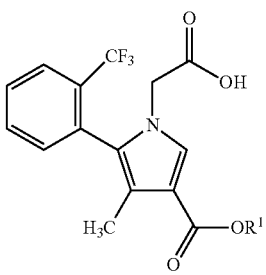

(C)

[wherein $R^1$ represents a C1-C4 alkyl group], characterized by using an optically active amine;

(9) the method according to the above (8), wherein the optically active amine is one compound selected from the group of the following compounds:

[Chem. 7]

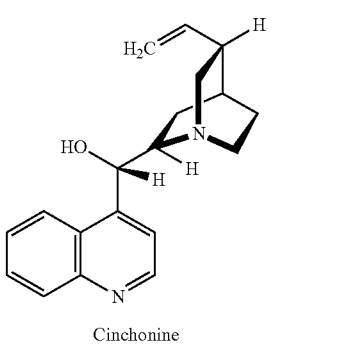

Cinchonine

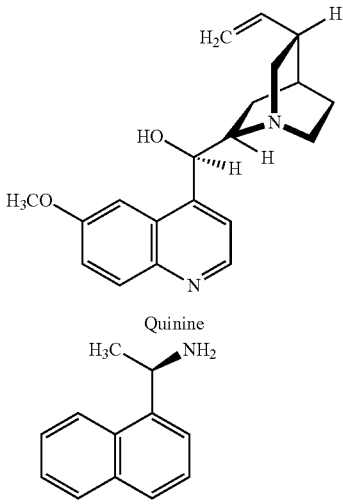

Quinine (R)-(+)-1-(1-Naphthyl)ethylamine;

(10) the method according to the above (8), wherein the optically active amine is (R)-(+)-1-(1-naphthyl)ethylamine;

(11) a method for producing the following intermediate compound (Ia):

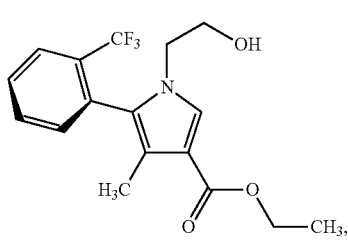

(Ia)

including:

(i) a step of obtaining an optically active amine salt of a desired atropisomer by resolving the following compound (C):

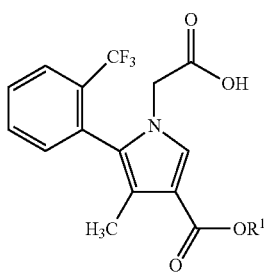

(C)

in a solvent using an optically active amine;

(ii) a step of removing the optically active amine from the optically active amine salt of the atropisomer obtained in (i) under a hydrochloric acid condition; and (iii) a step of reducing the atropisomer obtained in (ii) using a reducing agent;

(12) a method for producing ethyl (S)-1-(2-hydroxyethyl)-4-methyl-5-[2-(trifluoromethyl)-phenyl]-1H-pyrrole-3-carboxylate, including the following steps of:

(i) obtaining an optically active amine salt of (S)-2-[4-ethoxycarbonyl-3-methyl-2-[2-(trifluoromethyl)-phenyl]-1H-pyrrol-1-yl]acetic acid by resolving (RS)-2-[4-ethoxycarbonyl-3-methyl-2-[2-(trifluoromethyl)-phenyl]-1H-pyrrol-1-yl]acetic acid in a solvent using an optically active amine;

(ii) removing the optically active amine under an acidic condition; and thereafter (iii) performing reduction using a reducing agent;

(13) the method according to the above (11) or (12), wherein the reducing agent is sodium borohydride;

(14) the method according to any one selected from the above (11) to (13), wherein the optically active amine is quinine, cinchonine, or R-1-(1-naphthyl)ethylamine;

(15) the method according to any one selected from the above (11) to (13), wherein the optically active amine is cinchonine;

(16) the method according to any one selected from the above (11) to (15), wherein the solvent is an organic solvent;

(17) a method for producing the following compound (A):

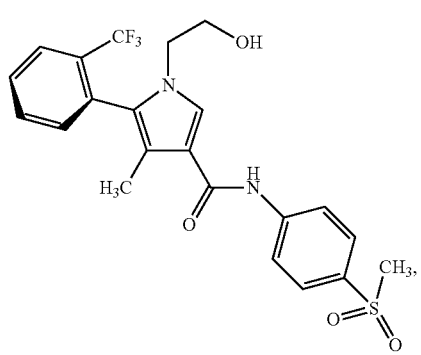

(A)

characterized by reacting ethyl (S)-1-(2-hydroxyethyl)-4-methyl-5-[2-(trifluoromethyl)-phenyl]-1H-pyrrole-3-carboxylate represented by the following formula (Ia):

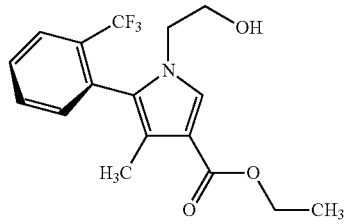

(Ia)

with 4-(methylsulfonyl)aniline in the presence of one reagent selected from a metal alkoxide and a Grignard reagent;

(18) the production method according to the above (17), wherein the reagent is a Grignard reagent;

(18-1) the production method according to the above (17), wherein the Grignard reagent is ethylmagnesium bromide;

(19) ethyl (S)-1-(2-hydroxyethyl)-4-methyl-5-[2-(trifluoromethyl) phenyl]-1H-pyrrole-3-carboxylate represented by the following formula (Ia):

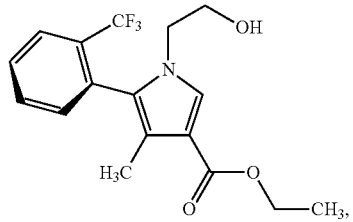

(Ia)

which is an intermediate for producing the following compound (A):

[Chem. 12]

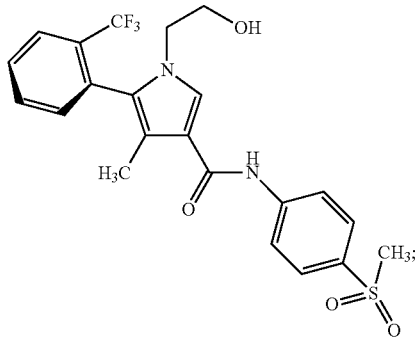

(A)

(20-0) a pyrrole compound represented by the following compound (C) or an atropisomer thereof:

[Chem. 14]

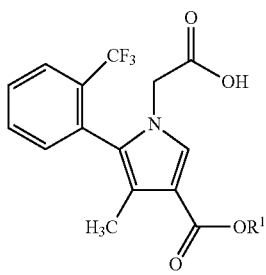

(C)

[wherein R¹ represents the same meaning as described above], which is an intermediate for producing (S)-1-(2-hydroxyethyl)-4-methyl-N-[4-(methylsulfonyl)-phenyl]-5-[2-(trifluoromethyl)phenyl]-1H-pyrrole-3-carboxamide;

(20-1) an optically active amine salt of (S)-2-[4-ethoxycarbonyl-3-methyl-2-[2-(trifluoromethyl)-phenyl]-1H-pyrrol-1-yl]acetic acid, which is an intermediate for producing (S)-1-(2-hydroxyethyl)-4-methyl-N-[4-(methylsulfonyl)phenyl]-5-[2-(trifluoromethyl)phenyl]-1H-pyrrole-3-carboxamide;

(20-2) the salt according to the above (20-1), wherein the optically active amine is one compound selected from cinchonine, quinine, and (R)-(+)-1-(1-naphthyl)ethylamine; and (20-3) the salt according to the above (20-1), wherein the optically active amine is (R)-(+)-1-(1-naphthyl)ethylamine.

(S)-1-(2-Hydroxyethyl)-4-methyl-N-[4-(methyl-sulfonyl)phenyl]-5-[2-(trifluoromethyl)phenyl]-1H-pyrrole-3-carboxamide represented by the following formula (A):

[Chem. 15]

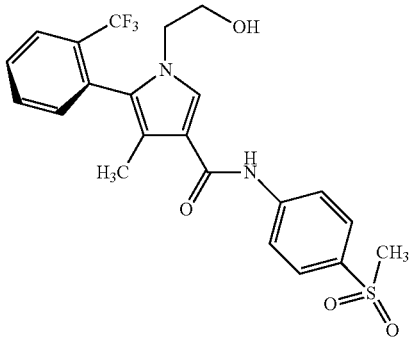

(A)

is sometimes referred to as Compound (A) in this description.

Examples of the "lipase" as used herein include Lipase AK "Amano" 20, Lipase A "Amano" 6, Lipase AS "Amano", a lipase derived from Candida Antarctica Type B, and a lipase derived from *Pseudomonas* sp. The lipase is preferably a lipase derived from *Pseudomonas* sp.

The "immobilized lipase" as used herein is a lipase which is brought into a state where its catalytic activity is maintained by immobilizing the lipase on a resin or confining the lipase in a small space so as to convert it to a solid form, and examples thereof include Chirazyme L-2 and Chirazyme L-2 carrier-fixed C3 (Roche) using a lipase derived from Candida Antarctica Type B, and Chirazyme L-6 *Pseudomonas* sp. and Novozyme 435 using a lipase derived from *Pseudomonas* sp. The immobilized lipase is preferably Novozyme 435.

Examples of the "protease" as used herein include Protease N "Amano" and Proleather FG "Amano", and further, the protease is preferably Protease N "Amano".

The "optically active amine" as used herein is preferably an amine compound having an asymmetric point such as quinine, cinchonine, (R)-1-(1-naphthyl)ethylamine, (R)-(+)-1-(4-chlorophenyl)ethylamine, or (R)-(+)-1-phenylethylamine, more preferably quinine, cinchonine, or (R)-1-(1-naphthyl)ethylamine, and particularly preferably cinchonine.

The "metal alkoxide" as used herein is preferably potassium t-butoxide, sodium t-butoxide, sodium methoxide or potassium ethoxide.

Examples of the "C1-C4 alkyl group" as used herein include methyl, ethyl, n-propyl, i-propyl, n-butyl, i-butyl, and t-butyl groups. The C1-C4 alkyl group as R¹ is preferably a methyl, ethyl, n-propyl, or i-butyl group, more preferably an ethyl group.

R¹ is preferably a methyl, ethyl, n-propyl, or i-butyl group, more preferably an ethyl group.

R² is preferably a 2-hydroxyethyl group.

The compound represented by the above general formula (B) is preferably ethyl (S)-1-(2-hydroxyethyl)-4-methyl-5-[2-(trifluoromethyl)phenyl]-1H-pyrrole-3-carboxylate represented by the above formula (Ia) or (S)-2-[4-ethoxycarbonyl-3-methyl-2-[2-(trifluoromethyl)-phenyl]-1H-pyrrol-1-yl]acetic acid, more preferably ethyl (S)-1-(2-hydroxyethyl)-4-methyl-5-[2-(trifluoromethyl)-phenyl]-1H-pyrrole-3-carboxylate.

A method for producing Compound (A) using the production intermediate compound of the present invention will be described in detail below.

Compound (A) can be produced by using known compounds as starting materials and using the following production method of the present invention and intermediates.

Step A: Production of Intermediate Compound (IV)

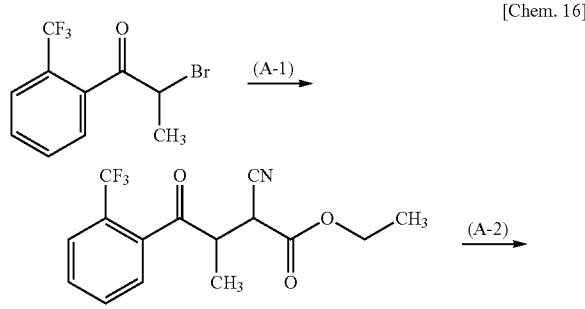

[Chem. 16]

Step B: Production of Intermediate Compound (Ia)

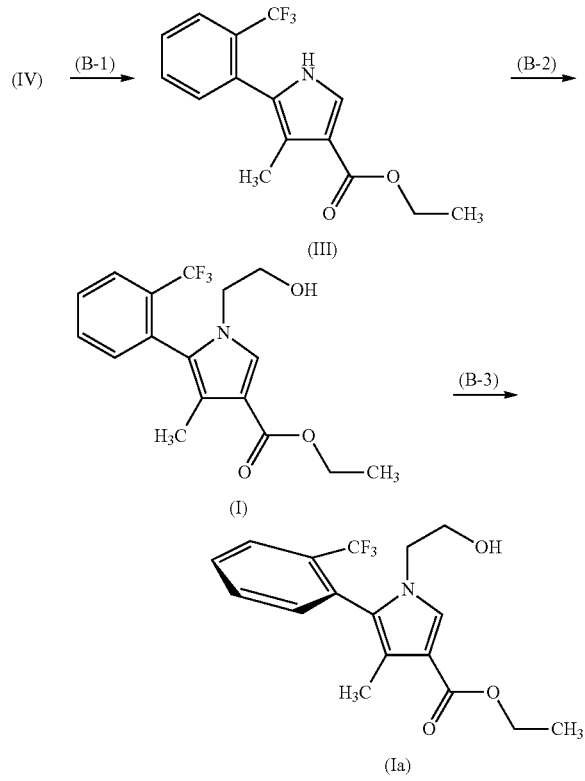

[Chem. 17]

Step C: Production of Intermediate Compound (Ia) through Intermediate Compound (IIa)

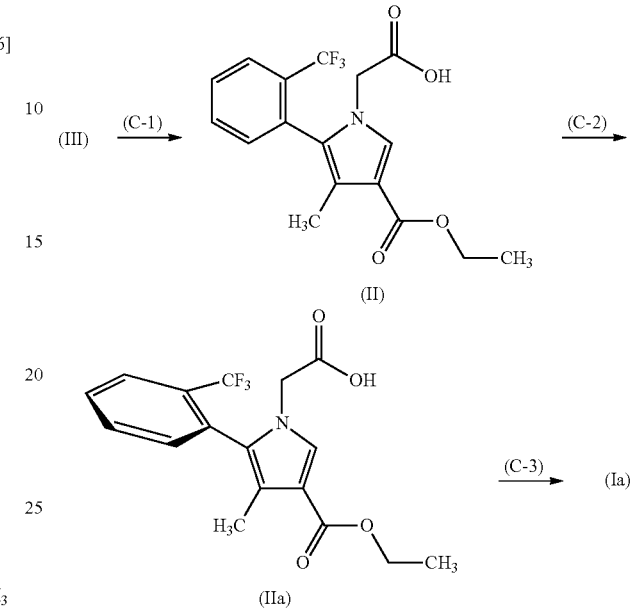

[Chem. 18]

Step D: Production of Compound (A)

[Chem. 19]

(Ia) $\xrightarrow{(D-1)}$ (A)

Hereinafter, the respective steps will be described.

(Step A-1)

This step is a step of producing Compound (V) by reacting 2-bromo-1-[2-(trifluoromethyl)phenyl]propan-1-one, which is a known substance, with ethyl cyanoacetate in the presence of a base.

As a solvent, an organic solvent which does not inhibit the reaction and dissolves the starting material to some extent is used. The solvent is preferably an amide such as methylacetamide.

Examples of the base include alkali metal carbonates such as potassium carbonate.

The reaction temperature is from 0° C. to 100° C., preferably from 40° C. to 60° C.

The reaction time is from 0.5 to 12 hours, preferably from 1 to 3 hours.

(Step A-2)

This step is a step of producing Compound (IV) by cyclizing Compound (V) to form a pyrrole ring.

As a solvent, an organic solvent which does not inhibit the reaction and dissolves the starting material to some extent is used. The solvent is preferably an aromatic hydrocarbon such as toluene.

As a reagent, it is preferred to blow hydrogen chloride gas in the presence of thionyl chloride, and further concentrated sulfuric acid may be added.

The reaction temperature is from 0° C. to 40° C., preferably room temperature.

The reaction time is from 1 to 30 hours, preferably from 10 to 20 hours.

(Step B-1)

This step is a step of producing Compound (III) by removing the chlorine group of Compound (IV).

As a solvent, a mixed solvent of water and an organic solvent which does not inhibit the reaction and dissolves the starting material to some extent is used. The solvent is preferably a mixed solvent of ethanol, tetrahydrofuran, and water.

As a reagent, sodium formate and a 5% palladium-carbon catalyst are preferred.

The reaction temperature is from 0° C. to 100° C., preferably from 40° C. to 60° C.

The reaction time is from 0.5 to 12 hours, preferably from 0.5 to 2 hours.

(Step B-2)

This step is a step of producing Compound (I) by introducing a hydroxyethyl group on the nitrogen atom of the pyrrole group of Compound (III) in a solvent in the presence of a base.

As the solvent, an organic solvent which does not inhibit the reaction and dissolves the starting material to some extent is used. The solvent is preferably an amide such as N,N-dimethylacetamide.

Examples of the base include metal alkoxides such as potassium t-butoxide and organic bases such as 4-dimethylaminopyridine.

A reagent for introducing a hydroxyethyl group is preferably bromoethanol or ethylene carbonate.

As a combination of the base and the reagent for introducing a hydroxyethyl group, a combination of 4-dimethylaminopyridine and ethylene carbonate is preferred.

The reaction temperature is from room temperature to 150° C., preferably from 100° C. to 120° C.

The reaction time is from 1 to 20 hours, preferably from 5 to 15 hours.

(Step B-3)

This step is a step of obtaining Compound (Ia) by optical resolution of an atropisomer through stirring of the above Compound (I) and a lipase or a protease in the presence of an acyl donor.

This method is usually performed in a solvent. The solvent is preferably a ketone such as acetone or methyl isobutyl ketone, an acetate ester such as isopropyl acetate, or a nitrile such as acetonitrile, more preferably a nitrile such as acetonitrile.

Examples of the lipase in this method include enzymes such as Lipase AK "Amano" 20, Lipase A "Amano" 6, and Lipase AS "Amano", and immobilized lipases such as Chirazyme L-2, Chirazyme L-2 carrier-fixed C3, Chirazyme L-6 *Pseudomonas* sp., and Novozyme 435. The lipase is preferably Novozyme 435.

The amount of the enzyme to be used in this method is preferably from 0.005 g to 1 g of the enzyme with respect to 1 g of a substrate, preferably 1 g of the enzyme, and the amount of the immobilized lipase to be used is preferably from 0.005 to 1 equivalent with respect to Compound (I).

The protease in this method is preferably Protease N "Amano".

The acyl donor in this method is preferably vinyl propionate, vinyl acetate, vinyl butyrate, vinyl laurate, or the like, and particularly preferably vinyl propionate.

The reaction temperature is from 0° C. to 50° C., preferably room temperature.

The enantiomeric excess of the obtained atropisomer can be determined according to conventional methods.

(Step C-1)

This step is a step of producing Compound (II) by introducing a carboxymethyl group on the nitrogen atom of the pyrrole group of Compound (III) in a solvent in the presence of a base using ethyl bromoacetate.

As the solvent, an organic solvent which does not inhibit the reaction and dissolves the starting material to some extent is used. The solvent is preferably an amide such as N,N-dimethylacetamide.

Examples of the base include metal alkoxides such as potassium t-butoxide.

The reaction temperature is from 0° C. to 100° C., preferably from 10° C. to room temperature.

The reaction time is from 0.5 to 12 hours, preferably from 1 to 3 hours.

(Step C-2)

This step is a step of producing Compound (IIa) by optical resolution of the atropisomer through stirring of Compound (II) and an optically active amine in a solvent.

This method is usually performed in a solvent. The solvent is preferably an acetate ester, a nitrile, a ketone, an ether, or a mixed solvent of a solvent selected therefrom and water, more preferably t-butyl methyl ether or di isopropyl ether.

In this method, the optically active amine is preferably one compound selected from quinine, cinchonine, R-1-(1-naphthyl)ethylamine, R-(+)-1-(4-chlorophenyl)-ethylamine, and R-(+)-1-phenylethylamine, more preferably R-1-(1-naphthyl)ethylamine, quinine, or cinchonine.

The amount of the optically active amine to be used in this method is preferably 0.5 equivalents with respect to Compound (II).

The reaction temperature is from room temperature to 50° C., preferably 50° C.

The diastereomeric excess of the obtained atropisomer can be determined according to conventional methods.

An amine salt of Compound (IIa) obtained in this step can also be converted to the free form using an acid. The acid to be used at this time is not particularly limited as long as it is an acid (an inorganic acid such as hydrochloric acid) usually used for removing an amine salt.

(Step C-3)

This step is a step of producing Compound (Ia) by reduction of the carboxymethyl group of Compound (IIa) to a hydroxyethyl group in the presence of boron trifluoride using a reducing agent.

As a solvent, a mixed solvent of water and an organic solvent which does not inhibit the reaction and dissolves the starting material to some extent is used. The solvent is preferably a mixed solvent of an ester such as ethyl acetate and water.

The reducing agent is not particularly limited as long as it is a reagent which reduces a carboxyl group to a hydroxymethyl group, but is preferably an alkali metal borohydride such as sodium borohydride.

The reaction temperature is from 0° C. to 100° C., preferably room temperature.

The reaction time is from 0.5 to 12 hours, preferably from 0.5 to 2 hours.

(Step D-1)

This step is a step of producing Compound (A) by reacting Compound (Ia) with 4-(methylsulfonyl)aniline in the presence of a Grignard reagent.

As the solvent, an organic solvent which does not inhibit the reaction and dissolves the starting material to some extent is used. The solvent is preferably an ether such as tetrahydrofuran.

The Grignard reagent is preferably a tetrahydrofuran solution of ethylmagnesium bromide, ethylmagnesium chloride, isopropylmagnesium chloride, methylmagnesium bromide, or phenylmagnesium bromide, more preferably a tetrahydrofuran solution of ethylmagnesium bromide.

The reaction temperature is from room temperature to 150° C., preferably from 60° C. to 100° C.

The reaction time is from 0.5 to 5 hours, preferably from 0.5 to 2 hours.

In this step, Compound (A) can also be produced by reacting Compound (Ia) with 4-(methylsulfonyl)aniline in the presence of a metal alkoxide such as potassium t-butoxide, sodium t-butoxide, sodium methoxide, or potassium ethoxide.

As a reaction solvent, an organic solvent which does not inhibit the reaction and dissolves the starting material to some extent is used. The solvent is preferably tetrahydrofuran, toluene, dimethyl sulfoxide, or N,N-dimethylacetamide.

The reaction temperature is from room temperature to 70° C., preferably from 40° C. to 70° C.

The reaction time is from 0.5 to 5 hours, preferably from 1 to 2 hours.

A racemate of a pyrrole compound represented by the following formula (B):

[Chem. 20]

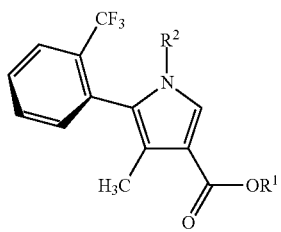

(B)

[wherein $R^1$ represents a C1-C4 alkyl group, and $R^2$ represents a 2-hydroxyethyl group or a carboxymethyl group] can be produced according to the above steps A and B.

A compound represented by the following formula (IB):

[Chem. 21]

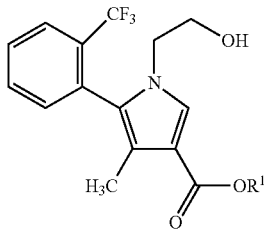

(IB)

[wherein $R^1$ represents a C1-C4 alkyl group] can be produced by alkylation of (RS)-1-(2-hydroxyethyl)-4-methyl-5-[2-(trifluoromethyl)phenyl]-1H-pyrrole-3-carboxylate produced in Example 6 under conventional conditions.

After completion of the reactions of the above-mentioned respective steps, the target compounds can be collected from the reaction mixture according to conventional methods. For example, the reaction mixture is appropriately neutralized, or in the case where insoluble matter is present, after the insoluble matter is removed by filtration, an organic solvent immiscible with water such as ethyl acetate is added thereto, followed by washing with water or the like. Thereafter, the organic layer containing the target compound is separated and dried over anhydrous magnesium sulfate or the like, and then, the solvent is distilled off, whereby the target compound can be obtained.

If necessary, the thus obtained target material can be separated and purified by conventional methods, for example, by appropriately combining recrystallization, reprecipitation, or a method conventionally used for separation and purification of an organic compound, for example, a method using a synthetic adsorbent such as adsorption column chromatography or partition column chromatography, a method using ion exchange chromatography, or normal-phase or reverse-phase column chromatography using silica gel or alkylated silica gel, and performing elution with a suitable eluent.

Compound (A) obtained according to the present invention can be used in a pharmaceutical or a pharmaceutical composition containing Compound (A) as an active ingredient.

The pharmaceutical containing Compound (A) as an active ingredient is preferably provided in the form of a pharmaceutical composition containing Compound (A) and one or more pharmaceutically acceptable carriers. The administration form of the pharmaceutical of the present invention is not particularly limited, and the pharmaceutical can be administered orally or parenterally, but is preferably administered orally.

The pharmaceutical composition containing Compound (A) as an active ingredient contains Compound (A) and a pharmaceutically acceptable carrier, and can be administered in the form of any of various injections through intravenous injection, intramuscular injection, subcutaneous injection, or the like, or through any of various methods such as oral administration or transdermal administration. The pharmaceutically acceptable carrier refers to a pharmaceutically acceptable material (for example, an excipient, a diluent, an additive, a solvent, etc.) which is involved in transport of Compound (A) from a given organ or viscus to another organ or viscus.

As a method for preparing a formulation, an appropriate formulation (for example, an oral preparation or an injection) is selected according to the administration method, and can be prepared by a conventionally used preparation method for various formulations. Examples of the oral preparation can include a tablet, a powder, a granule, a capsule, a pill, a troche, a solution, a syrup, an elixir, an emulsion, and an oily or aqueous suspension. In the case of an injection, a stabilizer, a preservative, a solubilizing agent, or the like can also be used in the formulation. It is also possible to form a solid preparation as a formulation to be prepared before use by placing a solution which may contain such a pharmaceutical aid or the like in a container, followed by lyophilization or the like. In addition, a single dosage may be packed in one container, or multiple dosages may be packed in one container.

Examples of a solid preparation include a tablet, a powder, a granule, a capsule, a pill, and a troche. These solid preparations may contain a pharmaceutically acceptable additive along with Compound (A). Examples of the additive include a filler, an expander, a binder, a disintegrant, a solubilization enhancer, a wetting agent, and a lubricant, and the solid preparation can be prepared by selecting an additive therefrom according to need and mixing.

Examples of a liquid preparation include a solution, a syrup, an elixir, an emulsion, and a suspension. These liquid preparations may contain a pharmaceutically acceptable additive along with Compound (A). Examples of the additive include a suspending agent and an emulsifying agent, and the liquid preparation can be prepared by selecting an additive therefrom according to need and mixing.

For example, in the case of a tablet, in the entire pharmaceutical composition, the content of a binder is generally from 1 to 10 parts by weight (preferably from 2 to 5 parts by weight), the content of a disintegrant is generally from 1 to 40 parts by weight (preferably from 5 to 30 parts by weight), the content of a lubricant is generally from 0.1 to 10 parts by weight (preferably from 0.5 to 3 parts by weight), and the content of a fluidizing agent is generally from 0.1 to 10 parts by weight (preferably from 0.5 to 5 parts by weight).

The pharmaceutical composition containing Compound (A) as an active ingredient can be administered to a warm-blooded animal (particularly a human being). The dose of Compound (A) or a pharmacologically acceptable salt thereof which is an active ingredient varies depending on the various conditions such as symptoms, age, and body weight of a patient, however, in the case of, for example, oral administration, it can be administered to a human being at a single dose of 0.1 mg/body to 20 mg/body (preferably 0.5 mg/body to 5 mg/body) one to six times per day depending on the symptoms.

Advantageous Effects of Invention

According to the present invention, a method for producing (S)-1-(2-hydroxyethyl)-4-methyl-N-[4-(methyl-sulfonyl)phenyl]-5-[2-(trifluoromethyl) phenyl]-1H-pyrrole-3-carboxamide (Compound (A)) having mineralocorticoid receptor antagonistic activity and a production intermediate compound thereof are provided. Compound (A) obtained according to the present invention has excellent stability and is useful as a pharmaceutical such as an antihypertensive drug.

DESCRIPTION OF EMBODIMENTS

Hereinafter, the present invention will be described in more detail by showing Examples of the present invention and the like, however, the scope of the present invention is not limited thereto.

EXAMPLES

Example 1

2-Bromo-1-[2-(trifluoromethyl)phenyl]propan-1-one

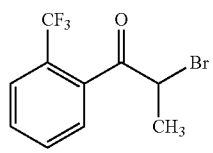

[Chem. 22]

To 1-[2-(trifluoromethyl)phenyl]propan-1-one (75 g (370 mmol)), t-butyl methyl ether (750 mL) and bromine (1.18 g (7.4 mmol)) were added. The resulting mixture was stirred at 15 to 30° C. for about 30 minutes, and after it was confirmed that the color of bromine disappeared, the mixture was cooled to 0 to 5° C. While maintaining the temperature at 0 to 10° C., bromine (59.13 g (370 mmol)) was added thereto, and the resulting mixture was stirred. After the mixture was stirred for about 2.5 hours, a 10 w/v % aqueous potassium carbonate solution (300 mL) was added thereto while maintaining the temperature at 0 to 25° C., and sodium sulfite (7.5 g) was further added thereto, followed by heating to 20 to 30° C. This solution was subjected to liquid separation, and to the obtained organic layer, water (225 mL) was added to wash the organic layer. Thereafter, the organic layer was concentrated under reduced pressure, whereby a t-butyl methyl ether solution (225 mL) of the title compound was obtained.

$^1$H NMR (400 MHz, CDCl$_3$) δ: 1.91 (3H, d, J=4.0 Hz), 4.97 (1H, q, J=6.7 Hz), 7.60-7.74 (4H, m.

Example 2

Ethyl 2-cyano-3-methyl-4-oxo-4-[2-(trifluoromethyl)phenyl]butanoate

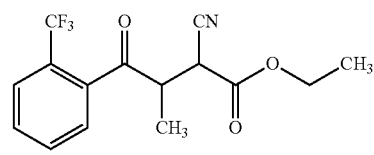

[Chem. 23]

To the 2-bromo-1-[2-(trifluoromethyl)phenyl]-propan-1-one/t-butyl methyl ether solution (220 mL) obtained in Example 1, dimethylacetamide (367 mL), ethyl cyanoacetate (53.39 g (472 mmol)), and potassium carbonate (60.26 g (436 mmol)) were sequentially added, and the resulting mixture was heated to 45 to 55° C. and stirred. After the mixture was stirred for about 2 hours, the mixture was cooled to 20 to 30° C., and then water (734 mL) and toluene (367 mL) were added thereto to effect extraction. Then, water (513 mL) was added to the resulting organic layer to wash the organic layer (washing was performed twice). Thereafter, the obtained organic layer was concentrated under reduced pressure, whereby a toluene solution (220 mL) of the title compound was obtained.

$^1$H NMR (400 MHz, CDCl$_3$) δ: 1.33-1.38 (6H, m), 3.80-3.93 (2H, m), 4.28-4.33 (2H, m), 7.58-7.79 (4H, m).

Example 3

Ethyl 2-chloro-4-methyl-5-[2-(trifluoro-methyl)phenyl]-1H-pyrrole-3-carboxylate

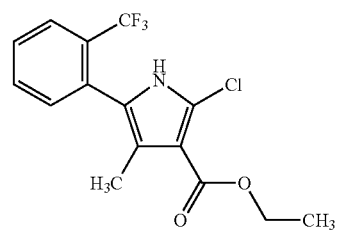

[Chem. 24]

To the toluene solution (217 mL) of ethyl 2-cyano-3-methyl-4-oxo-4-[2-(trifluoromethyl)phenyl]-butanoate obtained by the production method of Example 2, ethyl acetate (362 mL) and thionyl chloride (42.59 g (358 mmol)) were added at 20 to 30° C., and the resulting mixture was cooled to −10 to 5° C. Then, hydrogen chloride gas (52.21 g (1432 mmol)) was blown into the mixture, and concentrated sulfuric acid (17.83 g (179 mmol)) was further added thereto, and the resulting mixture was heated and stirred at 15 to 30° C. After the mixture was stirred for about 20 hours, ethyl acetate (1086 mL) was added thereto, followed by heating to 30 to 40° C., and water (362 mL) was added thereto, and then, the resulting mixture was subjected to liquid separation. To the organic layer obtained by liquid separation, water (362 mL) was added, followed by liquid separation, and then, a 5 w/v % aqueous sodium hydrogen carbonate solution (362 mL) was added thereto, followed by liquid separation.

Subsequently, the organic layer was concentrated under reduced pressure, and toluene (579 mL) was further added thereto, followed by concentration under reduced pressure, and then, toluene (72 mL) was added thereto, and the resulting mixture was cooled to 0 to 5° C. After the mixture was stirred for about 2 hours, the deposited crystal was filtered and washed with toluene (217 mL) cooled to 0 to 5° C. The obtained wet crystal product was dried under reduced pressure at 40° C., whereby the title compound was obtained (97.55 g, yield: 82.1%).

$^1$H NMR (400 MHz, CDCl$_3$) δ: 1.38 (3H, t, J=7.1 Hz), 2.11 (3H, s), 4.32 (2H, q, J=7.1 Hz), 7.39 (1H, d, J=7.3 Hz), 7.50-7.62 (2H, m), 7.77 (1H, d, J=8.0 Hz), 8.31 (1H, br).

Example 4

Ethyl 4-methyl-5-[2-(trifluoromethyl)phenyl]-1H-pyrrole-3-carboxylate

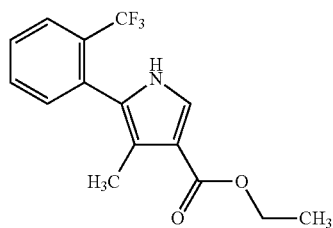

[Chem. 25]

To ethyl 2-chloro-4-methyl-5-[2-(trifluoromethyl)-phenyl]-1H-pyrrole-3-carboxylate (97.32 g (293 mmol)) obtained by the production method of Example 3, ethanol (662 mL), tetrahydrofuran (117 mL), water (49 mL), sodium formate (25.91 g (381 mmol)), and a 5% palladium-carbon catalyst (water content: 52.1%, 10.16 g) were added at room temperature, and the resulting mixture was heated to 55 to 65° C. and stirred. After the mixture was stirred for about 1 hour, the mixture was cooled to 40° C. or lower, and tetrahydrofuran (97 mL) and a filter aid (KC Flock, Nippon Paper Industries) (4.87 g) were added thereto. Then, the catalyst was filtered, and the residue was washed with ethanol (389 mL). The filtrate and the ethanol solution used for washing were combined, and the combined solution was concentrated under reduced pressure. Thereafter, water (778 mL) was added thereto and the mixture was stirred at 20 to 30° C. for 0.5 hours or more. The deposited crystal was filtered and washed with a mixed solution of ethanol/water=7/8 (292 mL). The thus obtained wet crystal product was dried under reduced pressure at 40° C., whereby the title compound was obtained (86.23 g, yield: 98.9%).

$^1$H NMR (400 MHz, CDCl$_3$) δ: 1.35 (3H, t, J=7.1 Hz), 2.18 (3H, s), 4.29 (2H, m), 7.40-7.61 (4H, m), 7.77 (1H, d, J=7.9 Hz), 8.39 (1H, br).

Example 5

Ethyl (S)-1-(2-hydroxyethyl)-4-methyl-5-[2-(trifluoromethyl) phenyl]-1H-pyrrole-3-carboxylate (5-1) Production Method 1
(5-1-1) Ethyl (RS)-1-(2-hydroxyethyl)-4-methyl-5-[2-(trifluoromethyl) phenyl]-1H-pyrrole-3-carboxylate

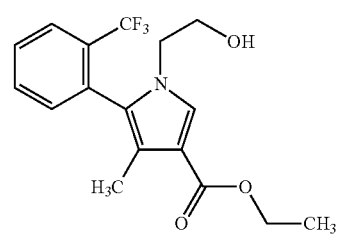

[Chem. 26]

To ethyl 4-methyl-5-[2-(trifluoromethyl)phenyl]-1H-pyrrole-3-carboxylate (65.15 g (219 mmol)) obtained by the production method of Example 4, N, N-dimethylacetamide (261 mL), ethylene carbonate (28.95 g (328.7 mmol)), and 4-dimethylaminopyridine (2.68 g (21.9 mmol)) were sequentially added at room temperature, and the resulting mixture was heated to 105 to 120° C. and stirred. After the mixture was stirred for about 10 hours, the mixture was cooled to 20 to 30° C., and toluene (1303 mL) and water (326 mL) were added thereto, and the organic layer was extracted. Then, water (326 mL) was added to the organic layer to wash the organic layer (washing was performed three times). The obtained organic layer was concentrated under reduced pressure, and ethanol (652 mL) was added thereto, and the resulting mixture was further concentrated under reduced pressure. Thereafter, ethanol (130 mL) was added thereto, whereby an ethanol solution (326 mL) of the title compound was obtained.

$^1$H NMR (400 MHz, CDCl$_3$) δ: 1.35 (3H, t, J=7.1 Hz), 1.84 (1H, broad singlet), 2.00 (3H, s), 3.63-3.77 (4H, m), 4.27 (2H, m), 7.35-7.79 (5H, m).

(5-1-2) (S)-Ethyl 1-(2-hydroxyethyl)-4-methyl-5-[2-(trifluoromethyl) phenyl]-1H-pyrrole-3-carboxylate After ethyl (RS)-1-(2-hydroxyethyl)-4-methyl-5-[2-(trifluoromethyl) phenyl]-1H-pyrrole-3-carboxylate (5.00 g (14.6 mmol)) produced according to (5-1-1) was dissolved by adding acetonitrile (50 mL) thereto, vinyl propionate (4.8 mL (43.9 mmol)) and an immobilized lipase, Novozyme 435 (Novozymes Japan Ltd.) (50 mg) were added thereto, and the resulting mixture was stirred at 20 to 30° C. for about 7 hours. After stirring, the immobilized lipase was filtered off, and the filtrate was concentrated under reduced pressure. Subsequently, the concentrated residue was dissolved by adding toluene (25 mL) thereto, and then, silica gel (for example, 60N, Kanto Chemical Co., Inc., spherical and neutral, 40 to 50 μm mesh was used) (10.00 g) was added thereto, and the resulting mixture was stirred for about 1 hour. After stirring, the silica gel was filtered with toluene (50 mL) (this filtrate was discarded), and subsequently, the silica gel was washed with ethyl acetate (50 mL), and the obtained filtrate was concentrated under reduced pressure. Then, to the obtained concentrated residue, toluene (10 mL) and ethylcyclohexane (10 mL) were added thereto, and the resulting mixture was cooled to −17 to −15° C. and stirred for 0.5 hours or more. Thereafter, ethylcyclohexane (100 mL) was slowly added thereto while keeping the temperature at −17 to −5° C., and the resulting mixture was stirred for 1 hour or more. The resulting crystal was filtered and washed with ethylcyclohexane (10 mL) cooled to −17 to −15° C., and the obtained wet crystal product was dried under reduced pressure, whereby the title compound (1.16 g) was obtained (yield: 23.2%). The enantiomeric excess of the obtained crystal was about 92.4% ee (calculated according to Example 5-1-3).

$^1$H NMR (400 MHz, CDCl$_3$) δ: 1.35 (3H, t, J=7.1 Hz), 1.84 (1H, broad singlet), 2.00 (3H, s), 3.63-3.77 (4H, m), 4.27 (2H, m), 7.35-7.79 (5H, m).

(5-1-3) HPLC Determination Method for Enantiomeric Excess

About 10 mg of a sample was collected and diluted with a mobile phase to 10 mL, whereby a sample solution was prepared.
Column: DAICEL CHIRALPAK AD-H (4.6 mm I.D.×250 mm)
Mobile phase: n-hexane: ethanol=95:5
Detection: UV 254 nm
Flow rate: about 1.0 mL/min
Column temperature: constant temperature of around 40° C.
Measurement time: about 10 min
Injection volume: 5 μL The enantiomeric excess was calculated according to the following formula using the peak area ratios of the S form (retention time: about 11 min) and the R form (retention time: about 9 min).

%ee={[(the peak area ratio of the title compound (S form))−(the peak area ratio of the R form)]÷ [(the peak area ratio of the title compound (S form))+(the peak area ratio of the R form)]}×100

(5-2) Production Method 2
(5-2-1) (RS)-2-[4-Ethoxycarbonyl-3-methyl-2-[2-(trifluoromethyl)-phenyl]-1H-pyrrol-1-yl]acetic acid

[Chem. 27]

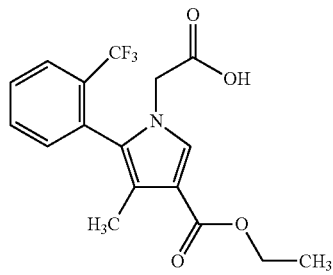

To ethyl 4-methyl-5-[2-(trifluoromethyl)phenyl]-1H-pyrrole-3-carboxylate (20.00 g (67.3 mmol)) produced according to Example 4, N,N-dimethylacetamide (190 mL) was added at room temperature, and subsequently, potassium t-butoxide (9.06 g (80.8 mmol)) was added thereto using N,N-dimethylacetamide (10 mL). After the resulting mixture was cooled to about 15° C., ethyl bromoacetate (9.0 mL (80.8 mmol)) was added thereto. After the resulting mixture was stirred for about 1 hour, a 5 N aqueous sodium hydroxide solution (27 mL) and water (40 mL) were added thereto, and the resulting mixture was stirred at room temperature for about 1 hour. Thereafter, water (300 mL) and ethyl acetate (200 mL) were added thereto, and the resulting mixture was stirred, followed by liquid separation. To the aqueous layer, ethyl acetate (400 mL) and 5 N hydrochloric acid (41 mL) were added to effect extraction, and the obtained organic layer was washed 5 times with water (100 mL) and further washed with a saturated sodium chloride solution (100 mL), and then dried over anhydrous sodium sulfate. The insoluble matter was filtered off, and the filtrate was concentrated under reduced pressure, and the resulting residue was purified by column chromatography (silica gel 200 g, methylene chloride/methanol =100/0 to 9/1), whereby (RS)-2-[4-ethoxycarbonyl-3-methyl-2-[2-(trifluoro-methyl)phenyl]-1H-pyrrol-1-yl]acetic acid (22.49 g, (63.3 mmol, yield: 94.1%)) was obtained.

On the other hand, in the case where purification is desired, it is also possible to isolate (RS)-2-[4-ethoxycarbonyl-3-methyl-2-[2-(trifluoromethyl)-phenyl]-1H-pyrrol-1-yl]acetic acid as an amine salt by using dicyclohexylamine. For example, (RS)-2-[4-ethoxycarbonyl-3-methyl-2-[2-(trifluoromethyl)phenyl]-1H-pyrrol-1-yl]-acetic acid (20.00 g (56.3 mmol)) was dissolved in diisopropyl ether (600 mL), and dicyclohexylamine (10.21 g (56.3 mmol)) was added thereto. After the resulting mixture was stirred at room temperature for about 24 hours, the deposited crystal was filtered and washed with diisopropyl ether (100 mL). The wet crystal product was dried under reduced pressure, whereby (RS)-2-[4-ethoxycarbonyl-3-methyl-2-[2-(trifluoromethyl)-phenyl]-1H-pyrrol-1-yl]acetic acid dicyclohexylamine salt (28.23 g (yield: 93.5%)) was obtained.

(5-2-2) (S)-2-[4-Ethoxycarbonyl-3-methyl-2-[2-(trifluoromethyl)phenyl]-1H-pyrrol-1-yl]acetic acid cinchonine salt (Entry 4 in Table 2)

(RS)-2-[4-Ethoxycarbonyl-3-methyl-2-[2-(trifluoromethyl)phenyl]-1H-pyrrol-1-yl]acetic acid (500.8 mg (1.41 mmol)) was dissolved by adding t-butyl methyl ether (7.5 mL) thereto at room temperature, and further cinchonine (207.8 mg (0.706 mmol)) was added thereto at room temperature, and the resulting mixture was stirred for about 19 hours. The deposited crystal was filtered and washed with t-butyl methyl ether (1.5 mL). The wet crystal product was dried under reduced pressure, whereby (S)-2-[4-ethoxycarbonyl-3-methyl-2-[2-(trifluoromethyl) phenyl]-1H-pyrrol-1-yl] acetic acid cinchonine salt (344.4 mg (yield: 37.6%)) was obtained. The diastereomeric excess of the obtained crystal was about 94.8% de.

$^1$H NMR (400 MHz, CDCl$_3$) δ: 0.80-0.94 (m, 1H), 1.26-1.40 (m, 3H), 1.50-2.23 (m, 7H), 2.51-2.53 (m, 1H), 2.98-3.39 (m, 4H), 3.96-4.55 (m, 5H), 5.05-5.26 (m, 2H), 5.91-6.00 (m, 1H), 6.12-6.15 (m, 1H), 6.57 (broad singlet), 6.91-7.19 (m, 2H), 7.24-7.95 (m, 8H), 8.03-8.11 (m, 1H), 9.00-9.11 (m, 1H).

(5-2-3) HPLC determination method for diastereomeric excess

About 10 mg of a sample is collected and diluted with a mobile phase to 10 mL, whereby a sample solution is prepared.
Column: DAICEL CHIRALCEL OD-RH (4.6 mm I.D.×150 mm)
Mobile phase: Mobile phase A: a 0.1 v/v % acetic acid solution:
acetonitrile=1:9
Mobile phase B: water: acetonitrile=2:8
Mobile phase A: Mobile phase B=1:1

Detection: UV 254 nm
Flow rate: about 1.0 mL/min
Column temperature: constant temperature of around 40° C.
Measurement time: about 10 min
Injection volume: 5 µL The diastereomeric excess was calculated according to the following formula using the peak area ratios of the S form (retention time: about 5 min) and the R form (retention time: about 4 min)

%de={[(the peak area ratio of the title compound
(S form))−(the peak area ratio of the R form)]÷
[(the peak area ratio of the title compound
(S form))+(the peak area ratio of the R
form)]}×100

(5-2-4) Effect of Optically Active Amine

After (RS)-2-[4-ethoxycarbonyl-3-methyl-2-[2-(trifluoromethyl)phenyl]-1H-pyrrol-1-yl]acetic acid (25 mg (0.07 mmol)) was dissolved in diisopropyl ether (0.5 mL), each of the various optically active amines (0.5 equivalents) was added thereto, and the resulting mixture was stirred at room temperature for about 19 hours. After stirring, the mixture was centrifuged, and the diastereomeric excess in the supernatant was determined by HPLC. The diastereomeric excess and yield of the precipitate (crystal, the target compound was in the S form) were calculated from the measured values (solubility and diastereomeric excess) of the supernatant and shown in Table 1.

TABLE 1

| Entry | Optically active amine | Supernatant % de | Precipitate % de | Yield (%) |
|---|---|---|---|---|
| 1 | (R)-(+)-1-phenylethylamine | 10 (R form) | 7 (S form) | 58.6 |
| 2 | (R)-(+)-1-(4-chlorophenyl)ethylamine | 19 (R form) | 22 (S form) | 46.7 |
| 3 | (R)-1-(1-naphthyl)ethylamine | 84 (R form) | 85 (S form) | 49.5 |
| 4 | quinine | 67 (R form) | 71 (S form) | 48.7 |
| 5 | cinchonine | 76 (R form) | 84 (S form) | 47.3 |

Among the optically active amines, high selectivity was observed in the case of R-1-(1-naphthyl)ethylamine, quinine, and cinchonine. On the other hand, in the case of R-(+)-1-(p-tolyl)ethylamine and cinchonidine, a different isomer (R form) was obtained as a precipitate.

Subsequently, by using cinchonine (0.5 equivalents), the type of solvent was examined, and the results are shown in Table 2. The amount of solvent was 15 times (v/v) the amount of sample, and the stirring time was about 19 hours at room temperature. The calculation methods for the diastereomeric excess and yield are the same as those for Table 1.

TABLE 2

| Entry | Solvent | % de | Yield (%) |
|---|---|---|---|
| 1 | isopropyl acetate | 98.5 | 23.5 |
| 2 | t-butyl acetate | 97.6 | 26.3 |
| 3 | cyclopentyl methyl ether | 97.1 | 30.7 |
| 4 | t-butyl methyl ether | 94.8 | 37.6 |

In each of the solvents, good results with respect to selectivity were obtained.

(5-2-5) Ethyl (S)-1-(2-hydroxyethyl)-4-methyl-5-[2-(trifluoromethyl)phenyl]-1H-pyrrole-3-carboxylate To an amine salt, for example, a R-1-(1-naphthyl) ethylamine salt of (S)-2-[4-ethoxy-carbonyl-3-methyl-2-[2-(trifluoromethyl) phenyl]-1H-pyrrol-1-yl]acetic acid (101.3 mg (0.19 mmol)), ethyl acetate (2 mL), water (0.5 mL), and 1 N hydrochloric acid (0.23 mL) were added at room temperature, and the resulting mixture was stirred, followed by liquid separation. The organic layer was washed with a saturated sodium chloride solution (0.5 mL), and then dried over anhydrous sodium sulfate. The insoluble matter was filtered off, and the filtrate was concentrated under reduced pressure. After the residue was dissolved by adding tetrahydrofuran (1 mL) thereto, sodium borohydride (22 mg, 0.582 mmol) was added thereto, and the resulting mixture was stirred at room temperature for about 1 hour. Subsequently, a boron trifluoride-ether complex (0.0586 mL, 0.48 mmol) was added thereto, and the resulting mixture was stirred for about 1 hour. The reaction mixture was subjected to an analysis by HPLC, the production ratio of the title compound was 97.7% (HPLC peak area ratio).

Example 6

(RS)-1-(2-Hydroxyethyl)-4-methyl-5-[2-(trifluoromethyl)phenyl]-1H-pyrrole-3-carboxylic acid

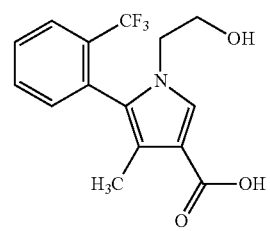

[Chem. 28]

To the solution of ethyl (RS)-1-(2-hydroxyethyl)-4-methyl-5-[2-(trifluoromethyl) phenyl]-1H-pyrrole-3-carboxylate/ethanol solution (321 mL) obtained by the production method of Example 5, water (128.6 mL) and sodium hydroxide (21.4 g (519 mmol)) were added at room temperature, and the resulting mixture was heated and stirred at 65 to 78° C. After stirring for about 6 hours, the mixture was cooled to 20 to 30° C., and water (193 mL) was added thereto, and then, the pH of the mixture was adjusted to 5.5 to 6.5 with 6 N hydrochloric acid while keeping the temperature at 20 to 30° C. To the mixture whose pH was adjusted, (RS)-1-(2-hydroxyethyl)-4-methyl-5-[2-(trifluoromethyl)-phenyl]-1H-pyrrole-3-carboxylic acid (6.4 mg) was added as a seed crystal, and water (193 mL) was further added thereto. Then, the mixture was cooled to 0 to 5° C., and again, the pH of the mixture was adjusted to 3 to 4 with concentrated hydrochloric acid, and the mixture was stirred for about 1 hour. Thereafter, the deposited crystal was filtered and washed with a 20% aqueous ethanol solution (93 mL) cooled to 0 to 5° C. The thus obtained wet crystal product was dried under reduced pressure at 40° C., whereby the title compound was obtained (64.32 g, yield: 95.0%).

[1]NMR (400 MHz, DMSO-$d_6$) δ: 1.87 (3H, s), 3.38-3.68 (4H, m), 7.43-7.89 (5H, m).

Example 7

(S)-1-(2-Hydroxyethyl)-4-methyl-5-[2-(trifluoromethyl)phenyl]-1H-pyrrole-3-carboxylic acid quinine Salt (7-1) (S)-1-(2-Hydroxyethyl)-4-methyl-5-[2-(trifluoromethyl)phenyl]-1H-pyrrole-3-carboxylic acid quinine salt Acetone (1,150 mL) was added to quinine (21.23 g (65.5 mmol)), and the resulting mixture was heated and stirred under reflux (about 50° C.). After it was confirmed that quinine was dissolved, (RS)-1-(2-hydroxyethyl)-4-methyl-5-[2-(trifluoromethyl)phenyl]-1H-pyrrole-3-carboxylic acid (41.00 g (130.9 mmol)) was added thereto using acetone (82 mL). After stirring for about 1 hour, the resulting mixture was slowly cooled to 0 to 5° C. (adequate cooling rate: about 0.3° C/min) and stirred for about 0.5 hours at that temperature. The resulting crystal was filtered and washed with acetone (205 mL) cooled to 0 to 5° C., whereby a crude wet crystal product (59.52 g) of the title compound was obtained (when a portion of the crude wet crystal product was dried under reduced pressure and the entire amount thereof was converted to a dry weight basis, the amount of the dry product was 35.35 g, and the yield was 42.2%). The diastereomeric excess of the obtained salt was about 94.8% de. Subsequently, to the obtained wet crystal product (59.52 g), ethanol (53 mL) and ethyl acetate (71 mL) were added, and the resulting mixture was heated and stirred under reflux (about 78° C.). After the mixture was stirred for about 1 hour, ethyl acetate (583 mL) was added thereto, and the resulting mixture was stirred under reflux again. Thereafter, the mixture was slowly cooled to 0 to 5° C. and stirred for about 0.5 hours at that temperature. The resulting crystal was filtered and washed with ethyl acetate (141 mL) cooled to 0 to 5° C. The obtained wet crystal product was dried under reduced pressure, whereby the title compound (32.48 g) was obtained (overall yield: 41.5%). The diastereomeric excess of the obtained salt was about 99.3% de.

$^1$H NMR (400 MHz, DMSO-$d_6$) δ: 1.87-1.89 (1H, m), 1.30-2.20 (9H, m), 2.41-2.49 (2H, m), 2.85-3.49 (6H, m), 3.65-3.66 (1H, m), 3.88 (3H, s), 4.82 (1H, broad singlet), 4.92-5.00 (2H, m), 5.23-5.25 (1H, m), 5.60 (1H, br), 5.80-6.00 (1H, m), 7.36-7.92 (9H, m), 8.67 (1H, d, J=4.6 Hz).

(7-2) HPLC determination for diastereomeric excess (ode) of (S)-1-(2-hydroxyethyl)-4-methyl-5-[2-(trifluoromethyl)phenyl]-1H-pyrrole-3-carboxylic acid quinine salt About 10 mg of a sample was collected and diluted with a mobile phase to 20 mL, whereby a sample solution was prepared.

Column: DAICEL CHIRALCEL OD-RH (4.6 mm I.D.×150 mm, 5 μm)

Mobile phase: a 0.1v/v % aqueous acetic acid solution (prepared by mixing 1 mL of acetic acid in 1000 mL of distilled water): acetonitrile=75:25

Detection: UV 220 nm

Flow rate: about 1.0 mL/min

Column temperature: constant temperature of around 40° C.

Measurement time: about 25 min

Injection volume: 5 μL

The diastereomeric excess (% de) was calculated according to the following formula using the peak area ratios of the S form (retention time: about 14.5 min) and the R form (retention time: about 15.5 min).

% de={[(the peak area ratio of the title compound
(S form))−(the peak area ratio of the R form)]÷
[(the peak area ratio of the title compound
(S form))+(the peak area ratio of the R
form)]}×100

Example 8

Ethyl (S)-1-(2-hydroxyethyl)-4-methyl-5-[2-(trifluoromethyl)phenyl]-1H-pyrrole-3-carboxylate (8-1) Production Method 1

To the (S)-1-(2-hydroxyethyl)-4-methyl-5-[2-(trifluoromethyl) phenyl]-1H-pyrrole-3-carboxylic acid quinine salt (32.00 g (50.2 mmol)) obtained in Example (7-1), ethyl acetate (480 mL) and a 2 N aqueous hydrochloric acid solution (160 mL) were added, and the resulting mixture was stirred, followed by liquid separation. The obtained organic layer was concentrated under reduced pressure (to 160 mL or less), ethyl acetate (160 mL) was added thereto, and the resulting mixture was further concentrated under reduced pressure. After completion of the concentration under reduced pressure, the amount of the liquid was adjusted (to 320 mL) by adding ethyl acetate, and the resulting mixture was cooled to 0 to 5° C. Subsequently, to this mixture, oxalyl chloride (11.2 mL (130.5 mmol)) was added while keeping the temperature at 0 to 10° C., and then, the resulting mixture was heated to 20 to 30° C. and stirred for about 1 hour. Ethanol (16 mL) was further added thereto, and the resulting mixture was heated and stirred under reflux for about 0.5 hours (about 78° C.) Thereafter, the mixture was cooled to 40° C. or lower, and a 5 w/v % aqueous sodium bicarbonate solution (160 mL) was added thereto, and the resulting mixture was stirred, followed by liquid separation. The resulting organic layer was concentrated under reduced pressure (to 96 mL), and methanol (160 mL) and a 5 w/v % aqueous sodium bicarbonate solution (64 mL) were added thereto, and the resulting mixture was stirred for 1 hour or more. Subsequently, toluene (800 mL) and a 20 w/v % aqueous sodium chloride solution (64 mL) were added thereto, and the resulting mixture was stirred, followed by liquid separation. To the resulting organic layer, a 20 w/v % aqueous sodium chloride solution (160 mL) was further added, and the resulting mixture was stirred, followed by liquid separation. The obtained organic layer was concentrated under reduced pressure (to 64 mL), and ethylcyclohexane (64 mL) was added thereto, and the resulting mixture was cooled to −17 to −15° C. and stirred for 0.5 hours or more. Thereafter, ethylcyclohexane (640 mL) was slowly added thereto while keeping the temperature at −17 to −5° C., and the resulting mixture was stirred for 1 hour or more. The resulting crystal was filtered and washed with ethylcyclohexane (64 mL) cooled to −17 to −15° C., and the obtained wet crystal product was dried under reduced pressure, whereby the title compound (14.20 g) was obtained (yield: 81.4%). The enantiomeric excess of the obtained crystal was about 99.3% ee (the enantiomeric excess was calculated according to Example (5-1-3)).

$^1$H NMR (400 MHz, CDCl$_3$) δ: 1.35 (3H, t, J=7.1 Hz), 1.84 (1H, broad singlet), 2.00 (3H, s), 3.63-3.77 (4H, m), 4.27 (2H, m), 7.35-7.79 (5H, m).

(8-2) Production Method 2

To the (S)-1-(2-hydroxyethyl)-4-methyl-5-[2-(trifluoromethyl)phenyl]-1H-pyrrole-3-carboxylic acid quinine salt (20.00 g (31.4 mmol)), ethyl acetate (300 mL) and a 2 N aqueous hydrochloric acid solution (100 mL) were added, and the resulting mixture was stirred, followed by liquid separation. The obtained organic layer was concentrated under reduced pressure. After completion of the concentration under reduced pressure, the resulting residue was dissolved by adding N,N-dimethylacetamide (50 mL) thereto, and then, potassium carbonate (6.51 g (47.1 mmol)) and ethyl iodide (3.0 mL (37.6 mmol)) were added thereto, and the resulting mixture was heated to about 60° C. and stirred for about 2 hours. Thereafter, the mixture was cooled to 40° C. or lower, and toluene (350 mL) was added thereto, and the resulting mixture was further cooled to 0 to 5° C. Subsequently, a saturated sodium chloride solution (100 mL) was added thereto, and the resulting mixture was heated to room temperature. Then, toluene (150 mL) and water (100 mL) were further added thereto, and the resulting mixture was stirred, followed by liquid separation. The obtained organic layer was washed by adding a saturated sodium chloride solution (100 mL), and then concentrated under reduced pressure.

Ethylcyclohexane (40 mL) was added thereto at room temperature, and the resulting mixture was cooled to −17 to −15° C. and stirred for 0.5 hours or more. Thereafter, a seed crystal was added thereto, and further ethylcyclohexane (400 mL) was slowly added thereto while keeping the temperature at −17 to −5° C., and the resulting mixture was stirred for 1 hour or more. The resulting crystal was filtered and washed with ethylcyclohexane (40 mL) cooled to −17 to −15° C., and the obtained wet crystal product was dried under reduced pressure, whereby the title compound (8.79 g) was obtained (yield: 82.10).

Example 9

(S)-1-(2-Hydroxyethyl)-4-methyl-N-[4-(methylsulfonyl) phenyl]-5-[2-(trifluoromethyl) phenyl]-1H-pyrrole-3-carboxamide Tetrahydrofuran (45 mL) was added to ethyl (S)-1-(2-hydroxyethyl)-4-methyl-5-[2-(trifluoromethyl)-phenyl]-1H-pyrrole-3-carboxylate (3.00 g (8.8 mmol)) obtained in Example 8 and 4-(methylsulfonyl) aniline (2.56 g (15.0 mmol)), and the resulting mixture was heated and stirred (60° C. or higher). To this liquid, a tetrahydrofuran solution of ethylmagnesium bromide (about 1 mol/L) (32.37 g (30.8 mmol)) was slowly added while keeping the temperature at 60° C. or higher. The resulting mixture was stirred for about 1 hour and then cooled to 0 to 5° C., and a 2 N aqueous hydrochloric acid solution (30 mL) and isobutyl acetate (75 mL) were added thereto, and the resulting mixture was stirred, followed by liquid separation. Subsequently, the resulting organic layer was washed with a 2 N aqueous hydrochloric acid solution (15 mL) (washing was repeated 4 times), and further washed with a 20 w/v % aqueous sodium chloride solution (30 mL). After the organic layer was concentrated under reduced pressure, the amount of the liquid was adjusted (to 30 mL) by adding isobutyl acetate, and the resulting mixture was stirred at room temperature for about 1 hour. Thereafter, the mixture was cooled to −15 to −10° C. and stirred for about 1 hour at that temperature. Thereafter, methylcyclohexane (15 mL) was added thereto, and the resulting mixture was further stirred for about 1 hour. The deposited crystal was filtered and washed with methylcyclohexane (12 mL) cooled to −15 to −10° C., and the obtained wet crystal product was dried under reduced pressure, whereby the title compound (3.90 g) was obtained (yield: 92.4%). The enantiomeric excess of the obtained crystal was about 99.8% ee.

Formulation Example 1

Capsule

The crystal (5 g) obtained in Example 9, lactose (115 g), cornstarch (58 g), and magnesium stearate (2 g) are mixed using a V-type mixer, and the resulting mixture is filled in a capsule (180 mg per capsule), whereby a capsule is obtained.

Formulation Example 2

Tablet

The crystal (5 g) obtained in Example 9, lactose (90 g), cornstarch (34 g), crystalline cellulose (20g), and magnesium stearate (1 g) are mixed using a V-type mixer, and the resulting mixture is tableted (a mass of 150 mg per tablet) using a tableting machine, whereby a tablet is obtained.

Formulation Example 3

Suspension

A dispersion medium in which methyl cellulose is dispersed or dissolved in purified water is prepared. The crystal obtained in Example 9 is weighed and placed in a mortar and kneaded well while adding the above-mentioned dispersion medium thereto in small portions, and then, purified water is added thereto, whereby a suspension (100 g) is prepared.

The invention claimed is:

1. A pyrrole compound represented by the formula (B):

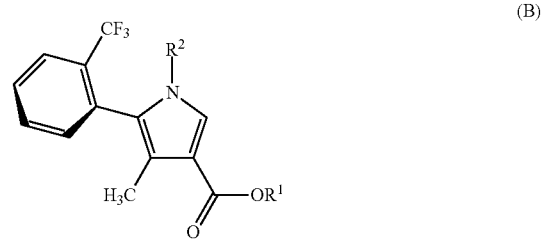

wherein $R^1$ represents a C1-C4 alkyl group, and $R^2$ represents a 2-hydroxyethyl group or a carboxymethyl group.

2. A compound according to claim 1, wherein $R^1$ is an ethyl group.

3. A compound according to claim 1, wherein $R^2$ is a 2-hydroxyethyl group.

4. A compound according to claim 1, wherein $R^2$ is a carboxymethyl group.

5. Ethyl (S)-1-(2-hydroxyethyl)-4-methyl-5-[2-(trifluoromethyl)phenyl]-1H-pyrrole-3-carboxylate represented by the formula (Ia):

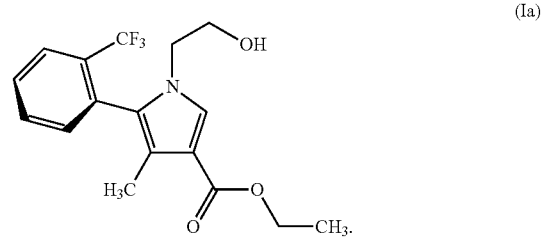

* * * * *

UNITED STATES PATENT AND TRADEMARK OFFICE
CERTIFICATE OF CORRECTION

PATENT NO. : 10,308,604 B2
APPLICATION NO. : 15/950973
DATED : June 4, 2019
INVENTOR(S) : M. Watanabe et al.

Page 1 of 1

It is certified that error appears in the above-identified patent and that said Letters Patent is hereby corrected as shown below:

In the Claims

| Column | Line | ERROR |
|---|---|---|
| 26 (Claim 2, Line 1) | 40 | "A compound" should read --The compound-- |
| 26 (Claim 3, Line 1) | 42 | "A compound" should read --The compound-- |
| 26 (Claim 4, Line 1) | 44 | "A compound" should read --The compound-- |

Signed and Sealed this
Eighteenth Day of February, 2020

Andrei Iancu
*Director of the United States Patent and Trademark Office*